(12) United States Patent
Warner

(10) Patent No.: US 6,602,414 B2
(45) Date of Patent: Aug. 5, 2003

(54) MOLECULE SEPARATION DEVICE AND METHOD COMBINING MULTIPLE FILTRATION MEDIA

(75) Inventor: Timothy Neal Warner, Downington, PA (US)

(73) Assignee: Formulations Pro, Yorba Linda, CA (US)

( * ) Notice: Subject to any disclaimer, the term of this patent is extended or adjusted under 35 U.S.C. 154(b) by 36 days.

(21) Appl. No.: 09/818,468

(22) Filed: Mar. 27, 2001

(65) Prior Publication Data

US 2001/0025818 A1 Oct. 4, 2001

Related U.S. Application Data

(60) Provisional application No. 60/198,529, filed on Apr. 20, 2000, and provisional application No. 60/193,118, filed on Mar. 30, 2000.

(51) Int. Cl.$^7$ ............................................. B01D 63/00
(52) U.S. Cl. .................. 210/321.75; 210/201; 210/202; 422/99; 422/101
(58) Field of Search ............. 422/99, 101; 210/321.75, 210/321.61, 638, 500.41, 500.27, 500.29, 500.1, 201, 202

(56) References Cited

U.S. PATENT DOCUMENTS

| | | | |
|---|---|---|---|
| 4,755,301 A | | 7/1988 | Bowers |
| 4,769,145 A | * | 9/1988 | Nakajima |
| 4,935,142 A | * | 6/1990 | Sternberg |
| 5,215,657 A | * | 6/1993 | Goldfield et al. |
| 5,368,729 A | * | 11/1994 | Stefkovich et al. |
| 5,490,927 A | * | 2/1996 | Herezeg |
| 5,733,449 A | * | 3/1998 | Bowers et al. |
| 5,792,425 A | * | 8/1998 | Clark et al. |
| 5,833,860 A | | 11/1998 | Kopaciewicz et al. |
| 5,861,094 A | * | 1/1999 | Goehde |
| 6,103,195 A | * | 8/2000 | Shukla et al. |
| 6,171,869 B1 | | 1/2001 | Safarian et al. |
| 6,221,655 B1 | * | 4/2001 | Fung et al. |

\* cited by examiner

Primary Examiner—Ana Fortuna
(74) Attorney, Agent, or Firm—Stetina Brunda Garred & Brucker

(57) ABSTRACT

A molecule separator device for isolating molecules having at least two separable properties and within a solution. The device includes a housing, and at least two molecule collection media disposed within the housing, whereby each such medium captures molecules exhibiting a respective property. In one embodiment, a first membrane captures only molecules with an ionic and/or hydrophobic and/or affinity attraction property while a second membrane captures only such molecules that additionally fall within a particular molecular weight range. A preferred housing is cylindrical for acceptance within a centrifuge, and is constructed of a plurality of releasably-connected compartments. The collection media is sequentially situated and centrifugation of the housing drives the solution through the media. Because of separation and subsequent collection in one device of molecules bearing multiple properties, the present invention permits rapid and efficient isolation of molecules and micro-particulate having a plurality of identification characteristics.

18 Claims, 3 Drawing Sheets

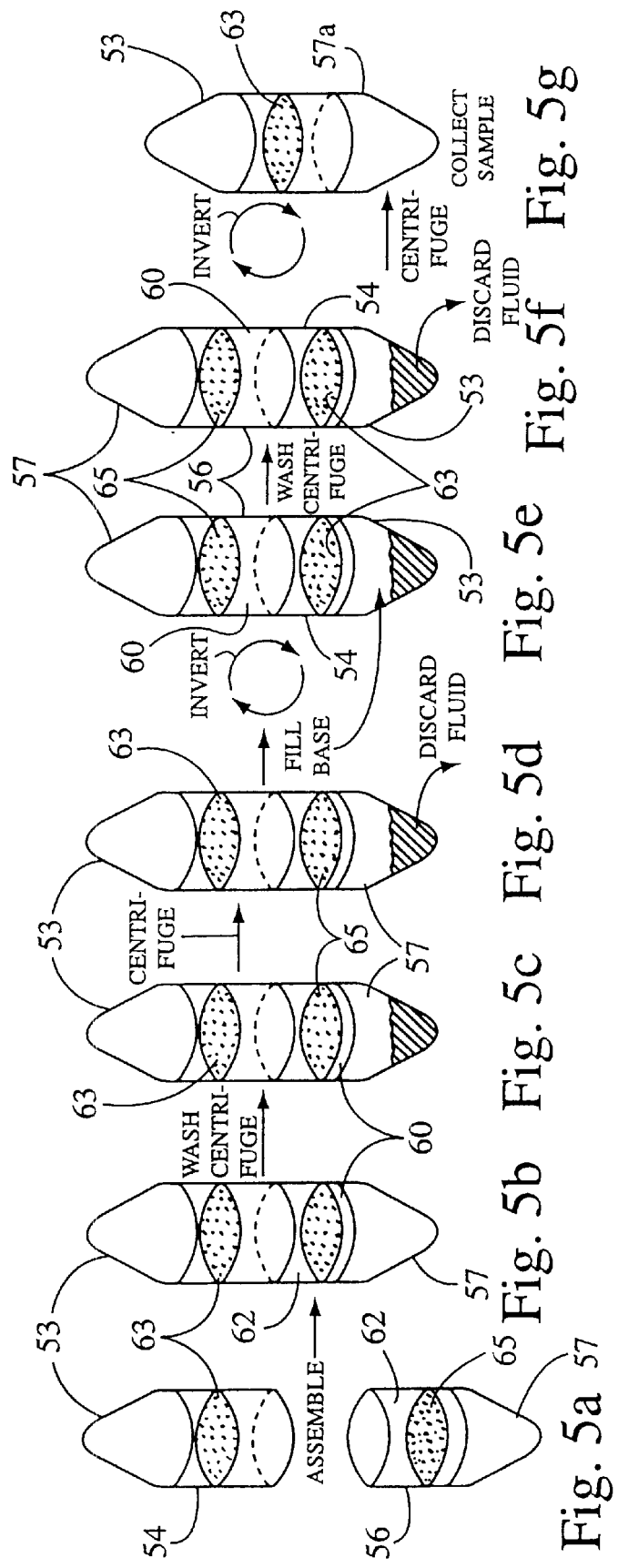

MOLECULE SEPARATION DEVICE AND METHOD COMBINING MULTIPLE FILTRATION MEDIA

CROSS REFERENCE TO RELATED APPLICATIONS

This application claims the benefits of U.S. Provisional Patent Application Ser. No. 60/193,118 filed Mar. 30, 2000, and of U.S. Provisional Patent Application Ser. No. 60/198,529 filed Apr. 20, 2000.

STATEMENT RE: FEDERALLY SPONSORED RESEARCH/DEVELOPMENT

Not Applicable

BACKGROUND OF THE INVENTION

This invention relates in general to the separation and capture of molecule types from a solution mixture thereof, and in particular to apparatus and methodology wherein molecules with two or more defined properties such as ionic, hydrophobic, or affinity attractions and molecular weight ranges are captured and retained first for one such property and thereafter for the additional property, with such respective collections accomplished sequentially in a single molecule separator device.

One of the most important tasks performed during research and other laboratory procedures is the separation of certain components from a mixture of components such that chemical or other analysis can proceed. A usual manner of accomplishing such separations is the employment of filtration devices whereby filtrate is collected by a filter medium as a solution containing the filtrate product passes through the filter medium. The most common of filter media are filter membranes and matrices thereof whose interstices prohibit, and thus capture, particulate whose physical size is too large to pass through as part of the solute.

While such filter membranes and related matrices (e.g. cloth) work well where particulate to be collected is defined only according to size and the interstices of the filter medium are adequately sized for filtrate retention, the separation of smaller particulate, as exemplified at the molecular level, requires much greater sophistication in order to accomplish separation and collection. Additionally, molecular separation many times involves the need to collect molecules that must possess at least two properties such as ionic, hydrophobic, or affinity attractions plus a limited molecular weight range. To accomplish separation and collection of such micro-particulate, multiple filtration devices must be employed where each device has a one-membrane-type filter for collecting filtrate having one defined characteristic from a solution. Once molecules are collected that possess the first desired property, the filtrate must be transferred to a second filtration device having a second one-membrane-type filter that addresses the second property and collects molecular filtrate meeting the second standard.

As is thus apparent, where, for example, molecules having at least two defining characteristics are to be isolated from a solution, a user must inefficiently perform filter procedures at least two separate times using at least two separate filtration devices. In view of this now-required inefficient approach, it is a primary object of the present invention to provide a molecule separator device where molecules having a plurality of properties can be separated and collected with one separator device.

Another object of the present invention to provide a molecule separator device where such molecule separation is accomplished sequentially within a single housing.

Yet another object of the present invention to provide a molecule separator device where respective dedicated membrane media provide filtrate collection.

Still another object of the present invention is to provide methodology for separating and capturing molecules having a plurality of properties utilizing a single separator device.

These and other objects of the present invention will become apparent throughout the description thereof which now follows.

BRIEF SUMMARY OF THE INVENTION

The present invention is a molecule separator device for separating and isolating molecules having at least two separable properties and present in a solution comprising the molecules. The separator device includes a housing for accepting pressured passage there through of the solution, and at least two molecule collection media disposed within the housing, wherein each such medium captures molecules exhibiting a respective property respectively capturable by the media. In a preferred embodiment, a first molecule-collection chromatography membrane captures and retains only molecules with an ionic, hydrophobic, or affinity attraction property while a second molecule-collection ultrafiltration membrane captures and retains additional such molecules that additionally fall within a particular molecular weight range. Conversely, these exemplary membranes can be in reverse order such that the first molecular collection membrane is an ultrafiltration membrane while the second membrane possesses the ionic, hydrophobic, or affinity attraction property. A preferred housing is generally cylindrical for operational acceptance within a generally cylindrical fixed-angle or swinging-bucket chamber of a centrifuge head, and is constructed of a plurality of liquid-tight, releasably-connected compartments in communication with each other. The collection media is situated in a sequential relationship among the compartments while centrifugation of the housing drives the solution through the media. Removing and replacing appropriate compartments during the molecule collection process permits separate and replaceable reservoir, wash, and collection sites to yield filtrate product as so chosen for further analysis, processing, or use, or for discard where a separation goal is the provision of clean solute. Because of separation and subsequent collection of molecules bearing two or more properties, the present invention permits rapid and efficient isolation of molecules and/or micro-particulate having multiple identification characteristics.

BRIEF SUMMARY OF THE DRAWINGS

An illustrative and presently preferred embodiment of the invention is shown in the accompanying drawings in which:

FIGS. 5a–5g illustrate use of the embodiment of FIG. 4.

DETAILED DESCRIPTION OF THE PREFERRED EMBODIMENTS

Figure 1:
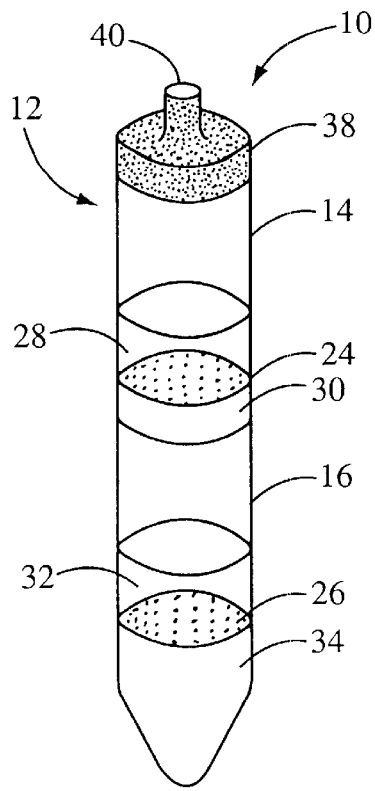
FIG. 1 is a perspective view of a first embodiment of a molecule separator device for capture or collection of molecules and/or micro-particulate.
Figure 2:
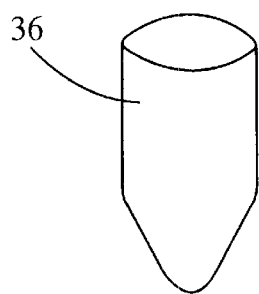
FIG. 2 is a perspective view of a separated compartment structure for the separator device of FIG. 1.

Referring first to FIGS. 1 and 2, a molecule separator device 10 is shown. The device 10 includes a housing 12 constructed of two releasably connected, liquid-tight, separable compartments 14, 16 attached to each other by conventional friction fit between adjacent compartments. Within the housing 12 are two sequentially disposed membranes 24, 26 for collecting filtrates. In particular, the first membrane 24 is a chromatography membrane operating as a cationic or anionic ion-exchange membrane, hydrophobic membrane, affinity membrane, or a combination thereof for attracting molecules exhibiting ionic and/or hydrophobic and/or affinity attractions. The first membrane 24 can have a porosity non-limitedly exemplified in the range of 0.1 to 10 microns and is fabricated of any appropriate microporous material including nylon, polycarbonate, polyethersulfone, glass fiber, polypropylene, polysulfone, cellulose acetate, regenerated cellulose, and mixed esters of cellulose or other polymeric material as would be recognized by a skilled artisan. The second membrane 26 preferably is anisotropic (asymmetrical) and can be fabricated of the same materials as the first while providing ultrafiltration in speaking toward molecular weight characteristics for capturing molecule filtrate. Thus, a chosen molecular weight range can be exemplified in values from about $5 \times 10^2$ to about $3 \times 10^6$ Daltons.

As shown in FIG. 1, the upper compartment 14 of the housing 12 has an upper reservoir chamber 28 immediately above the first membrane 24 and a lower reservoir chamber 30 immediately below the first membrane 24. The lower compartment 16 includes an upper chamber 32 immediately above the second membrane 26 and a fluid collection chamber 34 immediately beneath the second membrane 26. FIG. 2 shows an independent compartment 36 attachable to the upper compartment 14 during certain washing procedures as described later. The housing 12 can be constructed of a semi-rigid material such as polypropylene or of any other plastic or polymeric material as would be evident to a skilled artisan. Likewise, housing size can be as required to provide volumetric accommodations as required for a particular task. A screw-type closure cap 38 with an aperture 40 there through closes the housing 12. As is apparent, the housing 12 resembles the configuration of a standard centrifuge tube, thus permitting placement of the separator device 10 within a standard fixed-angle or swinging-bucket chamber (not shown) of a centrifuge head (not shown). While centrifugation is the preferred manner of pressurized force, the aperture 40 in the screw cap 38 is provided to accept a pressure nozzle such as the outlet of a hypodermic syringe (not shown) whose pressure can be applied to force the solution through the separator device 10.

Figures 3A, 3B, 3C, 3D, 3E:
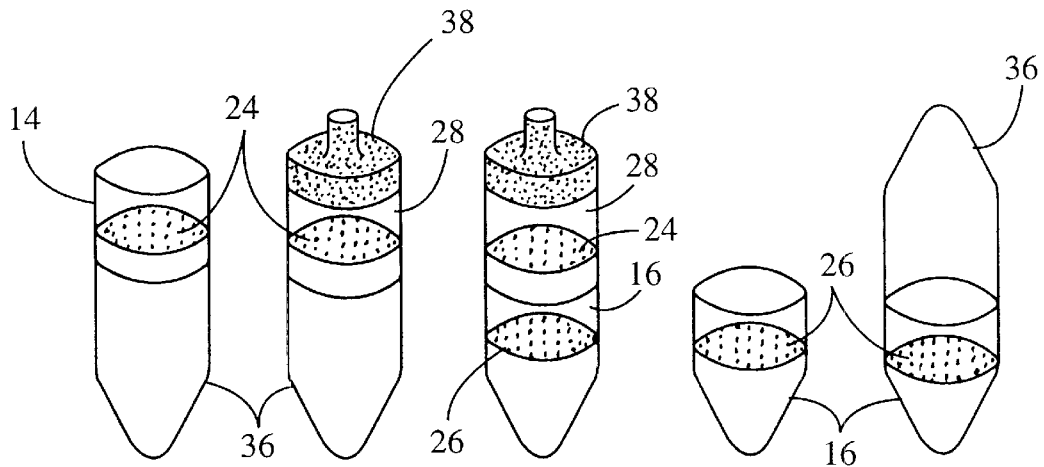
FIGS. 3a–3e illustrate use of the embodiment of FIG. 1.

A description of an exemplary operation of the separator device 10 is accompanied by the illustrations of FIGS. 3a–3e. First, the upper compartment 14 and an independent compartment 36 are attached as shown in FIGS. 3a. A subject solution is placed within the upper reservoir chamber 28 of upper the compartment 14, the cap 38 is secured in place as shown in FIG. 3b , and the resulting unit is centrifuged (fixed angle or swinging bucket) or pressurized for as long as necessary (many times about 0.5 minute) to accomplish liquid movement through the unit. As expected, the force moves the liquid quickly through the first membrane 24 as target molecules are collected. Since this first membrane 24 has a relatively large pore size, virtually any sized molecules or micro-particulate can pass through unimpededly, and only target molecules or micro particulate with ionic, hydrophobic, or affinity attractions will be retained. Alternatively, dependent upon the properties of the passing solution, target molecules or micro-particulate may pass through the membrane while contaminant is retained.

The cap 38 is removed, an appropriate buffer solution is added to the upper compartment 14 which is re-capped, and a second period of centriftigation or pressurization is completed to assure removal of any contaminants from the target molecules, while the molecules or micro-particulate remain bound to the first membrane 24. Elution of target molecules is accomplished as the independent compartment 36 with solute therein is removed and replaced with the lower compartment 16 as shown in FIG. 3c. The upper reservoir chamber 28 is then filled with an appropriate elution buffer to remove the target molecules from the first membrane 24 and the separator device 10 is centrifuged for several minutes as the target molecules now pass through the first membrane 24 are captured because of size by the second membrane 26. The upper compartment 14 (FIG. 3d) is removed and, thereafter, the upper reservoir chamber 32 is filled with a final washing buffer and centrifuged for several minutes for product desalting and placing the target molecules in a desired buffer such as physiological saline. Finally, an independent compartment 36 (FIG. 3e) is placed onto the compartment 16, and the resulting unit is inverted and centrifuged or pressurized for final product collection as the target molecules are forced from the second membrane 26 and into the independent compartment 36.

FIGS. 4 and 5a–5g show a second preferred embodiment and use of a molecule or micro-particulate separator device 50. In particular, the separator device 50 includes a housing 52 constructed of two releasably connected, liquid-tight, separable compartments 54, 56, each having one separable reservoir 53, 57, with compartments 54, 56 and reservoirs 53, 57 held to each adjacent structure by conventional friction fit. Within the housing 52 are two sequentially disposed membranes 63, 65 for collecting two different filtrates. In particular, the first membrane 63 is anisotropic (asymmetrical) and can be fabricated of any appropriate polymeric material with ultrafiltration pore size including nylon, polycarbonate, polyethersulfone, glass fiber, polypropylene, polysulfone, cellulose acetate, regenerated cellulose, and mixed esters of cellulose or polymeric materials as would be recognized by a skilled artisan while providing ultrafiltration in speaking toward molecular weight characteristics for capturing molecule filtrate. Thus, a chosen molecular weight range can be exemplified in values from about $5 \times 10^2$ to about $3 \times 10^6$ Daltons. The second membrane 65 is a chromatography membrane operating as a cationic or anionic ion-exchange membrane, hydrophobic membrane, affinity membrane, or a combination thereof for attracting molecules exhibiting ionic and/or hydrophobic and/or affinity attractions. The second membrane 65 can have a porosity non-limitedly exemplified in the range of 0.1 to 10 microns and is also fabricated of nylon, polycarbonate, polyethersulfone, polysulfone, cellulose acetate, glass fiber, polypropylene, regenerated cellulose, and mixed esters of cellulose or other polymeric materials.

Figure 4:
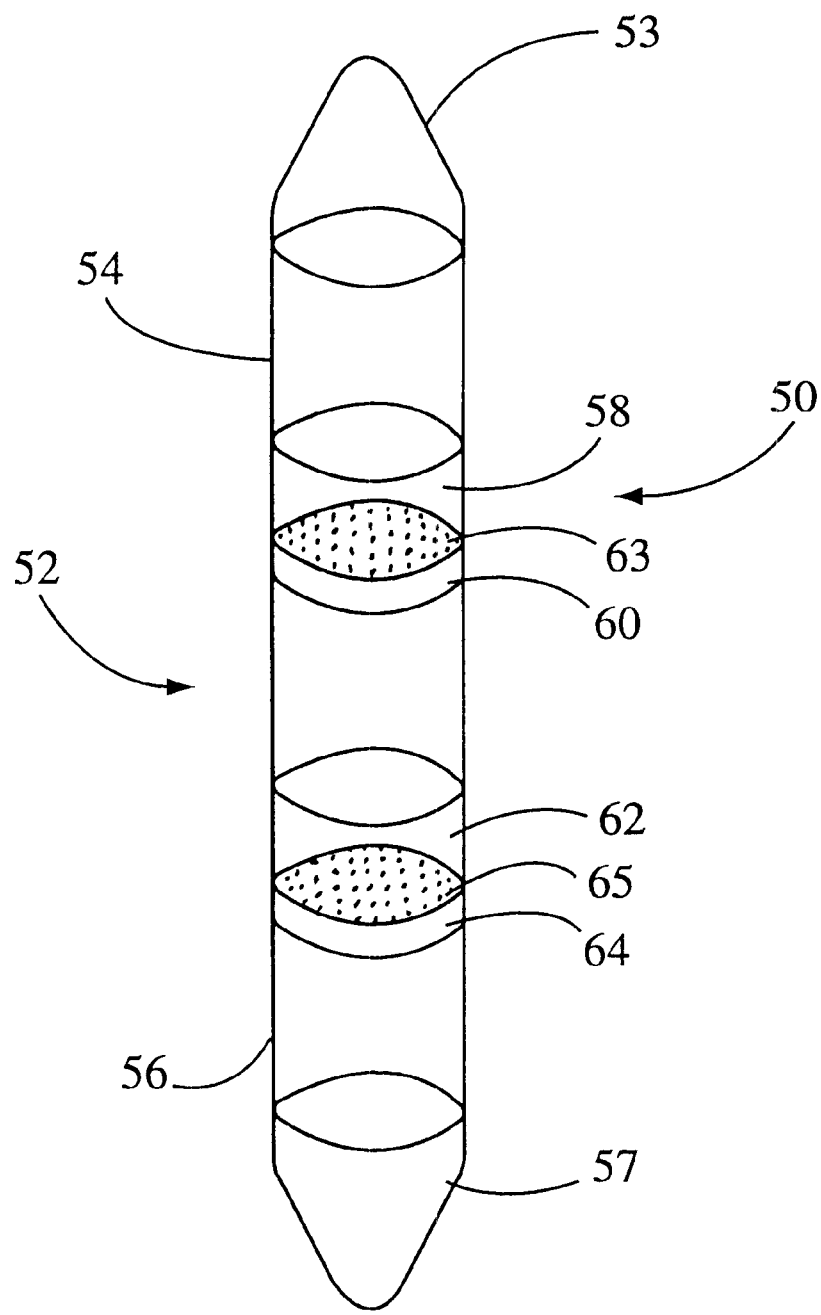
FIG. 4 is a side perspective view of a second embodiment of a molecule separator device.

As shown in FIG. 4, the upper compartment 54 of the housing 52 has an upper reservoir chamber 58 immediately above the first membrane 63 and a lower reservoir chamber 60 immediately below the first membrane 63. The lower compartment 56 includes an upper chamber 62 immediately above the second membrane 65 and a fluid collection chamber 64 immediately beneath the second membrane 65. The housing 52 can be constructed of a semi-rigid material such as polypropylene or of any other polymeric material as would be evident to a skilled artisan. Likewise, housing size can be as required to provide volumetric accommodations as required for a particular task. As is apparent, the housing 52 resembles the configuration of a standard centrifuge tube, thus permitting placement of the separator device 50 within a standard fixed-angle or swinging-bucket chamber (not shown) of a centrifuge head (not shown).

A description of an exemplary operation of the separator device 50 is accompanied by the illustrations of FIGS. 5a–5g. First, a subject solution is placed within the upper chamber 62 of the lower compartment 56 (FIG. 5a), the upper and lower compartments 54, 56 are attached as shown in FIG. 5b, and the resulting unit is centrifuged (fixed angle or swinging bucket) for as long as necessary (many times about 0.5 minute) to accomplish liquid movement through the membrane. As expected, the centrifugal force moves the liquid quickly through the second membrane 65 as target molecules are collected. Since this second membrane 65 has a relatively large pore size, virtually any sized molecule or micro-particulate can pass through unimpededly, and only target molecules with ionic or hydrophobic or affinity attractions will be retained. Alternatively, dependent upon the properties of the passing solution, target molecules or microparticulate may pass through the membrane while contaminant is retained. Next, an appropriate buffer solution is added to the upper chamber 62 of the lower compartment 56, and a second centrifugation is completed to assure removal of any contaminants from the target molecules while the molecules remain bound to the second membrane 65. The reservoir 57 is then removed and emptied, and filled with an elution buffer. Upon reassembly, the separator device 50 is inverted (FIG. 5e) and inserted into the centrifuge for centrifugation to remove the target molecules or microparticulate from the second membrane 65 and capture them because of size at the first membrane 63. Thereafter, while remaining in the now-upside down position, the lower reservoir chamber 60 is filled with an appropriate buffer to wash the target molecules free of high salt of the elution buffer while retaining the molecules at the first membrane 54. Finally, the reservoir 53 is emptied (FIG. 5f), the reservoir 57 is removed and replaced with a new reservoir 57a (FIG. 5g), and the resulting unit is inverted and centrifuged for final product collection as the target molecules are forced into the reservoir 57a. Alternatively, of course, the device 50 may be inverted at the beginning of the process such that the ultrafiltration membrane is the first contact membrane.

As is apparent, the molecule separator devices above described provide rapid two-stage separations within a single, convenient, and molecular-property specific apparatus. Additionally, as recognized by the skilled artisan, there are numerous possible combinations of chromatography membranes and ultrafiltration membranes for producing unique purification results. Therefore, while an illustrative and presently preferred embodiment of the invention has been described in detail herein, it is to be understood that the inventive concepts may be otherwise variously embodied and employed and that the appended claims are intended to be construed to include such variations except insofar as limited by prior art.

What is claimed is:

1. A molecule separator device for separation and isolating target molecules in a solution, the separator device comprising:
   a reversible first compartment, further comprising:
      a first molecule-collection medium operative to collect the target molecules with a first separation property; and
      two chambers immediately adjacent to two sides of the first molecule-collection medium; and
   a reversible second compartment connectible to and separable from the first compartment, the second compartment further comprising:
      a second molecule collection medium operative to collect the target molecules with a second separation property different from the first separation property; and
      two chambers immediately adjacent to two sides of the second molecule collection medium.

2. A molecule separator device as claimed in claim 1 wherein both the first and second molecule-collection media are membranes.

3. A molecule separator device as claimed in claim 1 wherein the first molecule collection-medium captures the target molecules exhibiting the first separation property of ion and/or hydrophobic and/or affinity attraction.

4. A molecule separator device as claimed in claim 3 wherein the second molecule-collection medium captures the target molecules exhibiting the second separation property of molecular weight property from about $5 \times 10^2$ to about $3 \times 10^6$ Daltons.

5. A molecule separator device as claimed in claim 1 wherein the second molecule-collection medium captures the target molecules exhibiting the second separation property of molecular weight property from about $5 \times 10^2$ to about $3 \times 10^6$ Daltons.

6. A molecule separator device as claimed in claim 5 wherein the second molecule-collection medium is fabricated of material selected from the group consisting of nylon, polycarbonate, polyethersulfone, polysulfone, glass fiber, polypropylene, cellulose acetate, regenerated cellulose, and mixed esters of cellulose.

7. A molecule separator device as claimed in claim 6 wherein the second molecule-collection medium is anisotropic.

8. A molecule separator device as claimed in claim 1 wherein the first and second molecule-collection media are disposed sequentially in relation to each other.

9. A molecule separator device as claimed in claim 1 wherein at least one of the first and second molecule-collection media are reversely disposed to collect the target molecules captured thereby.

10. A molecule separator device as claimed in claim 7 wherein at least one of the first and second molecule-collection media are reversely disposed to receive an elution solution for recollecting the captured molecules.

11. A molecule separator device as claimed in claim 3 wherein the first molecule-collection medium is at least an ion-exchange membrane, a hydrophobic membrane, an affinity membrane or a combination of any two or all three thereof.

12. A molecule separator device as claimed in claim 11 wherein the first molecule-collection medium is fabricated of material selected from the group consisting of nylon, polycarbonate, polyethersulfone, polysulfone, glass fiber, polypropylene, cellulose acetate, regenerated cellulose, and mixed esters of cellulose.

13. A molecule separator device as claimed in claim 12 wherein the second molecule-collection medium is fabricated of material selected from the group consisting of nylon, polycarbonate, polyethersulfone, polysulfone, glass fiber, polypropylene, cellulose acetate, regenerated cellulose, and mixed esters of cellulose.

14. A molecule separator device as claimed in claim 1 wherein the first and second reversible compartments are connected to form a generally cylindrical liquid-tight housing for operational acceptance within a generally cylindrical fixed-angle or swinging-bucket chamber of a centrifuge head.

15. A molecule separator device as claimed in claim 14 wherein the first and second compartments are in communication with each other while being connected to form the housing.

16. A molecule separator device as claimed in claim 15 wherein the housing additionally comprises a releasably-connected cap with an aperture there through for receiving a fluid or gas pressurization nozzle.

17. A molecule separator device for separation and isolating target molecules in a solution, the separator device comprising:

a first compartment, further comprising:
 a first molecule collecting medium operative to collect the molecules with a first separation property; and
 two chambers immediately adjacent to two sides of the first molecule collecting medium;

a second compartment liquid-tight connectible to and separable from the first compartment, the second compartment further comprising:

a second molecule collecting medium operative to collect the molecules with a second separation property different from the first separation property; and
 two chambers immediately adjacent to two sides of the second molecule collecting medium; and an reversible independent chamber, liquid-tight connectible to the first and second compartments.

18. A molecule separator device as claimed in claim 17 wherein the first molecule-collection medium includes a chromatography membrane, and the second molecule-collection medium includes a weight ultrafiltration membrane.

* * * * *